United States Patent
Walsh et al.

(10) Patent No.: US 9,429,673 B2
(45) Date of Patent: Aug. 30, 2016

(54) SURFACE-BASED NMR MEASUREMENT

(71) Applicant: VISTA CLARA INC., Mukilteo, WA (US)

(72) Inventors: David O. Walsh, Mukilteo, WA (US); Elliot D. Grunewald, Seattle, WA (US); Hong Zhang, Kenmore, WA (US)

(73) Assignee: VISTA CLARA INC., Mukilteo, WA (US)

( * ) Notice: Subject to any disclaimer, the term of this patent is extended or adjusted under 35 U.S.C. 154(b) by 527 days.

(21) Appl. No.: 14/034,110

(22) Filed: Sep. 23, 2013

(65) Prior Publication Data
US 2014/0084927 A1 Mar. 27, 2014

Related U.S. Application Data

(60) Provisional application No. 61/704,395, filed on Sep. 21, 2012.

(51) Int. Cl.
| | | |
|---|---|---|
| *G01V 3/14* | (2006.01) | |
| *G01N 24/08* | (2006.01) | |
| *G01R 33/38* | (2006.01) | |

(52) U.S. Cl.
CPC .............. *G01V 3/14* (2013.01); *G01N 24/081* (2013.01); *G01R 33/3808* (2013.01)

(58) Field of Classification Search
CPC ... G01V 3/14; G01N 24/081; G01R 33/3808
See application file for complete search history.

(56) References Cited

U.S. PATENT DOCUMENTS

| | | | |
|---|---|---|---|
| 4,714,881 A * | 12/1987 | Givens | G01V 3/32 324/303 |
| 5,055,788 A | 10/1991 | Kleinberg | |
| 6,091,241 A | 7/2000 | Querleux | |
| 6,160,398 A | 12/2000 | Walsh | |
| 6,291,994 B1 | 9/2001 | Kim | |
| 6,828,892 B1 | 12/2004 | Fukushima | |
| 7,095,230 B2 | 8/2006 | Blümich | |
| 7,391,215 B2 | 6/2008 | Callaghan | |
| 7,466,128 B2 | 12/2008 | Walsh | |
| 7,733,091 B2 | 6/2010 | Marble | |
| 7,986,143 B2 | 7/2011 | Walsh | |
| 8,148,986 B2 | 4/2012 | Driesel | |
| 8,581,587 B2 | 11/2013 | Walsh et al. | |
| 2002/0084783 A1* | 7/2002 | Blumich | G01R 33/28 324/322 |
| 2006/0186882 A1* | 8/2006 | Walsh | G01R 33/3415 324/309 |
| 2008/0284426 A1* | 11/2008 | Shorey | G01N 24/081 324/307 |
| 2011/0109311 A1 | 5/2011 | Walsh | |
| 2011/0160563 A1* | 6/2011 | Glogau | A61B 5/055 600/410 |
| 2011/0241667 A1* | 10/2011 | Blumich | G01N 24/08 324/303 |
| 2013/0187647 A1 | 7/2013 | Walsh | |

(Continued)

OTHER PUBLICATIONS

Paetzold, "Surface Soil Water Content Measurement Using Pulsed Nuclear Magnetic Resonance Techniques", Article, 4 pages, 1985.

*Primary Examiner* — Rodney Bonnette
(74) *Attorney, Agent, or Firm* — Nathaniel A. Gilder; Jensen & Puntigam, PS

(57) ABSTRACT

Technologies applicable to surface-based NMR measurement are disclosed. A surface probe is positionable at or above a surface of the Earth and adapted to make NMR measurements of shallow or very shallow subsurface volumes. NMR spectrometer components connected to the surface probe are configured to control electromagnetic pulses produced by the surface probe and to record resulting detected NMR signals from the subsurface volume.

30 Claims, 10 Drawing Sheets

(56) References Cited

U.S. PATENT DOCUMENTS

2013/0193969 A1 8/2013 Grunewald
2013/0293228 A1 11/2013 Walsh
2014/0009148 A1 1/2014 Walsh

* cited by examiner

SURFACE-BASED NMR MEASUREMENT

CROSS REFERENCE TO RELATED APPLICATIONS

Priority is claimed to U.S. Provisional Patent Application No. 61/704,395, filed on 21, Sep. 2012, entitled "NMR MEASUREMENT APPARATUS AND METHOD CHARACTERIZING THE SUBSURFACE," the disclosure of which is incorporated herein by reference in its entirety.

BACKGROUND

Nuclear Magnetic Resonance (NMR) systems have been in use for many years and can be used to provide imaging and/or analysis of a sample being tested. For example, U.S. Pat. No. 6,160,398, U.S. Pat. No. 7,466,128, U.S. Pat. No. 7,986,143, U.S. patent application Ser. No. 12/914,138, and U.S. patent application Ser. No. 13/104,721 describe a variety of NMR technologies, and are incorporated herein by reference. Various different types of NMR include medical NMR, often referred to as Magnetic Resonance Imaging (MRI), and NMR for measuring properties of earth formations, which provides, for example, geophysical techniques for detecting properties of the earth's crust or earthen structures. This disclosure relates to the latter type of NMR, and so the term "NMR" as used herein refers to NMR in the geophysical context. While there is some overlap in the technologies that may be applied in MRI and NMR, the samples being measured and the environments in which measurements are performed are different, leading to many differences in the technologies applied.

In general, NMR measurement involves generating a static magnetic field within a sample volume, emitting Radio-Frequency (RF) electromagnetic pulses into the sample volume, and detecting RF NMR responses from the sample volume. Most commonly, NMR measurement involves emitting multiple RF pulses in rapid succession and measuring the RF NMR responses between the RF pulses. The measured RF NMR responses provide useful information about the sample volume.

NMR measurements may be used to estimate properties including, for example, the abundance of hydrogen contained within a sample volume as well as moisture content, porosity, permeability, and pore-size distribution of the sample volume. The measurement may also be used to determine fluid composition and fluid diffusion properties. NMR measurements may further be used to detect certain other atomic species, including carbon and potassium.

NMR has been applied as a geophysical technique using two primary approaches. In the first approach of downhole logging NMR, an NMR measurement apparatus is lowered into a borehole in the earth, and NMR measurements are performed to determine properties within and/or surrounding the borehole. The logging apparatus contains permanent magnets that create a static magnetic field for the NMR measurement, and one or more coils or antenna used to excite an NMR signal from fluids in the Earth formation and to measure this NMR response. A second approach, Earth's Field Surface NMR (EF-SNMR) utilizes Earth's natural geomagnetic field as the static magnetic field and one or more coils or antenna deployed on Earth's surface to excite and measure the NMR response of subsurface fluids.

While the two geophysical approaches have certain advantages, neither approach is ideal for rapidly obtaining information about the properties of the shallow or very shallow subsurface. The shallow subsurface is herein defined as any portion of the subsurface within about the upper 10 meters of the subsurface, that is, between the surface at zero meters depth to about 10 meters below the surface. The very shallow subsurface is herein defined as any portion of the subsurface within about the upper 2 meters of the subsurface, that is, between the surface at zero meters depth to about 2 meters below the surface. Logging NMR measurements offer high signal-to-noise, and because they produce a strong gradient in the static magnetic field, can use gradient imaging techniques to obtain information with high spatial resolution and precision. Logging NMR measurements, however, require the installation of a borehole and so cannot be used without disturbing the subsurface. EF-SNMR measurements are less invasive because they can be used to assess properties of a fluid bearing Earth formation without installing a borehole or well. EF-SNMR measurements, however, are limited by a very low signal-to-noise for two reasons. First, the NMR signal amplitude is proportional to the square of the static magnetic field strength and so is proportionally small in the Earth's weak magnetic field. Secondly, the NMR signal diminishes as the volume of material contributing to the measurement diminishes and so EF-SNMR measurements typically include measurements with large coils over large and deep volumes. Further, because the Earth's magnetic field is very uniform, EF-SNMR cannot take advantage of gradient imaging techniques and so may suffer from poor spatial resolution capabilities.

SUMMARY

Technologies applicable to surface-based NMR measurement are disclosed. Some example surface-based NMR measurement apparatus may include a surface probe positionable at or above a surface of the Earth or earthen structure, and adapted to make NMR measurements of shallow or very shallow subsurface volumes under the surface, and NMR spectrometer components connected to the surface probe and configured to control radio frequency electromagnetic pulses produced by the probe and to record resulting detected NMR signals from the subsurface volume.

Example surface probes may include, inter alia, static magnetic field generating devices and an array of one or more electromagnetic field devices. The static magnetic field generating devices, may comprise, e.g., permanent magnets arranged so as to generate a static magnetic field in shallow or very shallow subsurface volumes under the surface and substantially under the surface probe. The array of electromagnetic field devices may comprise, e.g., an induction coil or antenna arranged to transmit radio frequency electromagnetic pulses to cause a precession of NMR spins within the subsurface volume, and arranged to detect NMR signals produced by the precession of NMR spins in the static magnetic field in the subsurface volume.

In some embodiments, the permanent magnets and induction coil may be arranged within the at least one surface probe so that when the surface probe is positioned at or above the surface, the induction coil defines a plane parallel to the surface and also parallel to the orientation of the static magnetic field at the center of the induction coil. In some embodiments, the surface probe and NMR spectrometer components may be adapted within a portable housing or a vehicle for the surface-based NMR measurement apparatus, and the surface probe may be positioned substantially at a bottom of the portable housing or vehicle.

Some example surface-based Nuclear Magnetic Resonance (NMR) measurement methods may include positioning a surface probe as described herein at or above a surface of the Earth, substantially over a shallow or very shallow subsurface volume of interest, and activating NMR spectrometer components connected to an array in the surface probe to: transmit radio frequency electromagnetic pulses by the array into the subsurface volume to cause a precession of NMR spins within a subsurface volume; and record NMR signals produced by the precession of NMR spins in the static magnetic field in the subsurface volume. In some embodiments, methods may include activating the NMR spectrometer multiple times to acquire measurements of multiple subsurface volumes at different depths. In some embodiments, methods may include moving a portable housing or vehicle while activating the NMR spectrometer components multiple times to make multiple surface-based NMR measurements of multiple subsurface volumes as the portable housing or vehicle moves.

Further aspects and variations are discussed in detail below.

BRIEF DESCRIPTION OF THE DRAWINGS

Various features and attendant advantages of the disclosed technologies will become fully appreciated when considered in conjunction with the accompanying drawings, in which like reference characters designate the same or similar parts throughout the several views, and wherein.

DETAILED DESCRIPTION

Figure 1:
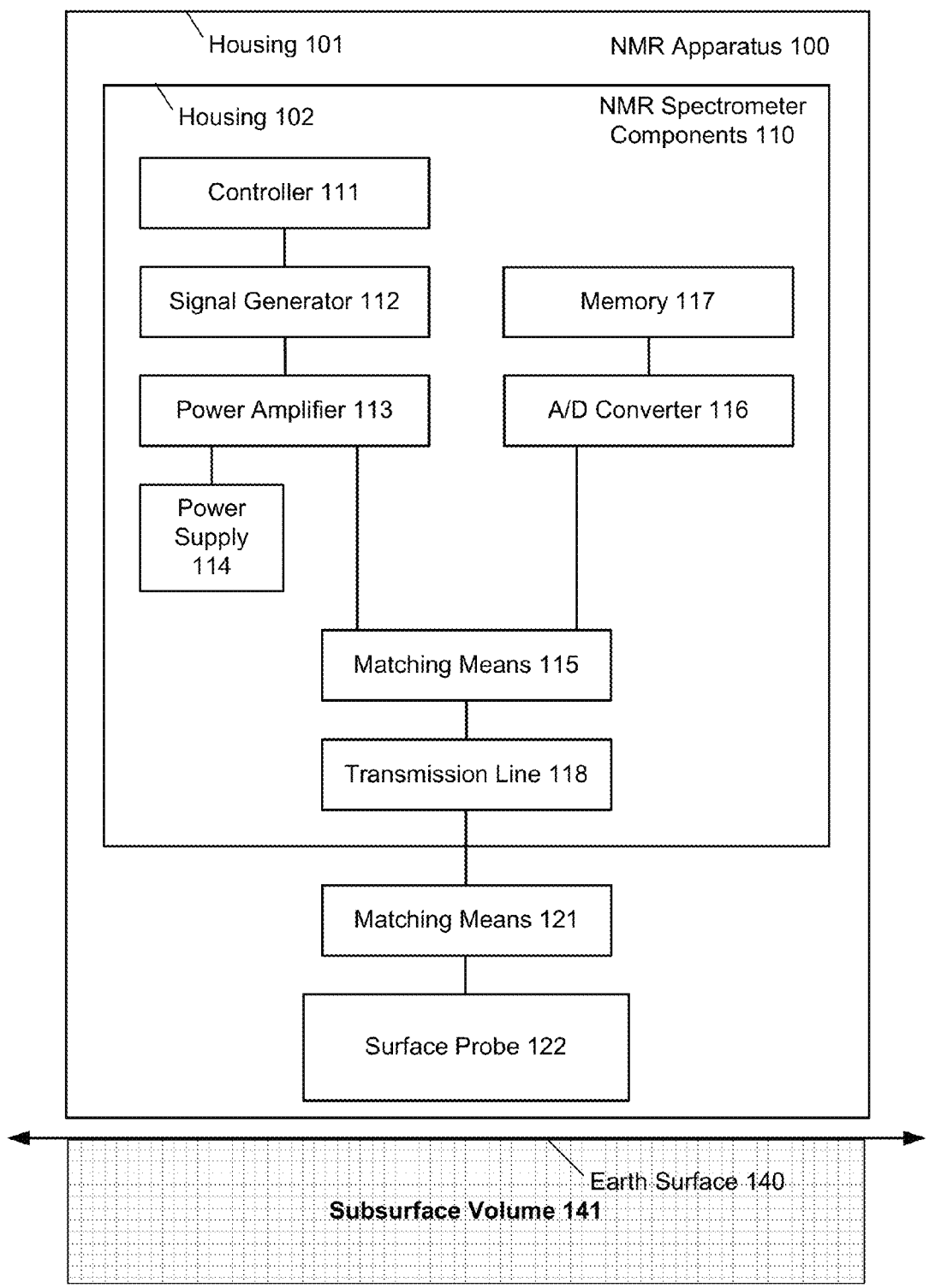
FIG. 1 illustrates an example surface-based NMR measurement apparatus and example locations of components thereof relative to the surface of the earth.

Prior to explaining embodiments of the invention in detail, it is to be understood that the invention is not limited to the details of construction or arrangements of the components and method steps set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

Technologies including, inter alia, apparatus and methods applicable to surface-based NMR measurement are disclosed herein. A surface probe is positionable at or above a surface of the Earth and adapted to make NMR measurements of shallow or very shallow subsurface volumes. NMR spectrometer components connected to the surface probe are configured to control electromagnetic pulses produced by the surface probe and to record resulting detected NMR signals from the subsurface volume.

In some embodiments, the surface probe and NMR spectrometer components may be included in a surface-based NMR measurement apparatus positionable at or above a surface of the Earth. The term "positionable at or above a surface of the Earth," as used herein, is defined as not including components such as magnets or borehole probes requiring insertion into or under the surface of the Earth to effectively perform NMR measurements. In some embodiments surface-based NMR measurement apparatus that are "positionable at or above a surface of the Earth" may also conveniently have a shape and structure, e.g., of a housing or vehicle in which the surface-based NMR measurement apparatus may be contained, that allows stable positioning of the surface-based NMR measurement apparatus, on a surface of the Earth, in an orientation that allows effective NMR measurements of the subsurface.

The terms "surface of the Earth," and "subsurface volume," as used herein refer to both natural and man-made surfaces, and subsurface volumes underneath such surfaces, respectively. It will be appreciated that disclosed surface-based NMR measurement apparatus and methods may be applied on both natural, unmodified Earth surfaces such as in fields, on mountainsides, etc., and on man-made structures such as dams, levees, roads, etc.

The term "shallow subsurface volume," as used herein refers to a subsurface volume that is within about the upper 10 meters of the subsurface, that is, between the surface at zero meters depth to about 10 meters below the surface, as noted in the background section. The term "very shallow subsurface volume," as used herein refers to a subsurface volume that is within about the upper 2 meters of the subsurface, that is, between the surface at zero meters depth to about 2 meters below the surface, as also noted in the background section. Surface-based NMR measurement apparatus may be arranged for NMR measurements in shallow or very shallow subsurface volumes by, inter alia, adjusting dimensions of electromagnetic field devices used in surface probes. For example, induction coils of about 2 meters in diameter or less may be used to make NMR measurements of very shallow subsurface volumes, while induction coils of about 10 meters or less in diameter may be used to make NMR measurements of shallow subsurface volumes. Some embodiments may be arranged for NMR measurements in even shallower subsurface volumes, e.g., induction coils of about 1.5 feet in diameter or less may be used to make NMR measurements of extremely shallow subsurface volumes, within about the upper 1 foot of the subsurface, e.g., subsurface volumes that may be within the upper 1, 2, or several inches below the surface.

In some embodiments, surface-based NMR measurement apparatus may include a surface probe and NMR spectrometer components within a portable housing or a vehicle. The surface probe may be positioned substantially at a bottom of the portable housing or vehicle, while the NMR spectrometer components may be positioned anywhere within the portable housing or a vehicle as convenient for particular embodiments. In some embodiments, the surface probe may be housed separately from NMR spectrometer components, allowing repositioning the surface probe without necessarily repositioning the NMR spectrometer components.

Example surface probes described herein may include static magnetic field generating devices. The static magnetic field generating devices may comprise, e.g., permanent magnets arranged so as to generate a static magnetic field in shallow or very shallow subsurface volumes under the surface and substantially under the surface probe. It will be appreciated that alternatives to permanent magnets, such as electromagnets, are available to those of skill in the art, and such alternatives may be included in some embodiments. This disclosure generally references permanent magnets as example static magnetic field generating devices, however, the term "static magnetic field generating devices" is not limited to permanent magnets.

Permanent magnets in a surface probe may be arranged so as to generate a static magnetic field in subsurface volumes under the surface and substantially under the surface probe. Static magnetic fields may be of any strength or direction, as desired for particular embodiments. Magnetic field strength may be controlled by adjusting a number and/or strength of permanent magnets. Magnetic field direction may be controlled by adjusting permanent magnet positions and orientations.

Some embodiments may include a permanent magnet array, the permanent magnet array comprising one or more permanent magnets with polarity directed perpendicular to the surface, in a direction toward or away from the surface. For example, a permanent magnet array may include a single permanent magnet with polarity directed perpendicularly toward the surface, or a single permanent magnet with polarity directed perpendicularly away from the surface. Alternatively, a permanent magnet array may comprise at least one permanent magnet with polarity directed toward the surface, and at least one permanent magnet with polarity directed away from the surface. In another arrangement, the permanent magnet array may include the permanent magnets with polarities directed toward and away from the surface along with at least one permanent magnet with polarity directed parallel to the surface. Still further, some embodiments may include a metallic plate positioned between static magnetic field generating devices and parallel to the surface, wherein the metallic plate focuses the known static magnetic field in the subsurface volume.

Example surface probes described herein may also include static magnetic field generating devices. The electromagnetic field devices may comprise, e.g., induction coils. It will be appreciated that alternatives to induction coils, such as antennae or magnetometers, are available to those of skill in the art, and such alternatives may be included in some embodiments. This disclosure generally references induction coils as example electromagnetic field devices, however, the term "electromagnetic field devices" is not limited to induction coils.

Some induction coils in a surface probe may be arranged to transmit electromagnetic pulses to cause a precession of NMR spins within subsurface volumes. Some induction coils in a surface probe may be arranged to detect NMR signals produced by the precession of NMR spins in the known static magnetic field in the subsurface volumes. Induction coils for transmitting electromagnetic pulses and detecting NMR signals may comprise separate transmitting and detecting coils in some embodiments, or dual purpose transmitting and detecting coils. Various example induction coil arrangements are provided in the drawings provided herewith.

In some embodiments, permanent magnets and induction coil(s) may be arranged within a surface probe so that when the surface probe is positioned at or above the surface, the induction coil defines a plane parallel to the surface and also parallel to the orientation of the known static magnetic field at the center of the induction coil. As a result, electromagnetic fields from the induction coils may be substantially perpendicular to the static magnetic field within the subsurface volume. "Substantially perpendicular" as used herein includes angles which may be within about 45 degrees of perpendicular. Embodiments in which the induction coil defines a plane not parallel to the surface and/or not parallel to the orientation of the static magnetic field at the center of the induction coil are also feasible, and may produce electromagnetic fields which are other than substantially perpendicular to the static magnetic field. Such non-perpendicular embodiments may nonetheless produce electromagnetic fields which have some perpendicular component, and may utilize perpendicular components of generated electromagnetic fields to activate NMR processes, and may be adapted to adjust NMR measurements to account for the strength of perpendicular components of generated electromagnetic fields.

NMR spectrometer components may be connected to the induction coil(s) in the surface probe, and configured to control electromagnetic pulses in the induction coil(s) and to record detected NMR signals from the subsurface volume. Example NMR spectrometer components in surface-based NMR measurement apparatus may generally comprise components enabling the excitation, detection and recording of NMR processes. NMR spectrometer components may generally include a controller or computer, a signal generator, a power amplifier, and a power supply. The controller may be configured to cause the signal generator, power amplifier, and power supply to generate current and/or voltage waveforms which, when transmitted to the surface probe, produce NMR activating pulses or sequences of pulses.

NMR spectrometer components may also include one or more sets of receive electronics configured for detection and recording of NMR voltage signals induced on the induction coils. The various components of the receive electronics may include some or all of the following: tuning circuits, passive or active transmit/receive switches, preamplifiers, impedance matching circuits, RF demodulation means, filters, Analog to Digital (A/D) converters, and digital storage devices or memory.

NMR spectrometer components may be connected to the induction coil(s) in the surface probe via transmission lines of arbitrary length that couple a power amplifier output and/or a set of receive electronics to induction coils in the surface probe, through optional arbitrary matching circuits. Impedance matching circuits or other impedance matching means may be configured to match an output impedance of the power amplifier through a transmission line to a load impedance of an induction coil.

In some embodiments, a surface probe may comprise a preamplifier configured to amplify NMR signals detected at an induction coil. An output impedance of the preamplifier may be matched to a characteristic impedance of a transmission line configured to transmit detected NMR signals from the induction coil to the NMR spectrometer components. A/D converter(s) may also be located at an induction coil/surface probe side of the transmission line. Electronics within the surface probe may be coupled with a power supply, or may comprise a local power supply such as one or more batteries.

In some embodiments, one or more surface probes may be configured within housings separate from NMR spectrometer components. A plurality of surface probes may be coupled with NMR spectrometer components via a plurality of transmission lines, and the NMR spectrometer components may be configured to perform NMR measurements with the plurality of surface probes. A switching device may be coupled between the plurality of transmission lines and the power amplifier, and the switching device may be configured to selectively connect the power amplifier to one or more of the transmission lines.

In some embodiments, additional NMR measurement sensors may be coupled with NMR spectrometer components to measure local noise electromagnetic fields, to assist in cancellation of such noise field sources from NMR signal data detected with the surface probe(s). In some embodiments, noise may be recorded on a reference channel separate from surface probe channel(s). In some embodiments, noise cancellation may be accomplished in software. In some software-based noise cancellation methods, noise cancellation may be accomplished by cancelling correlated portion(s) of the noise between the reference channels and the primary detection (surface probe) channels.

In some embodiments, surface-based NMR measurement apparatus may include active or passive Q-damping means to reduce the Q-factor of the surface probe, immediately following transmitted pulses, allowing a reduction of wait times between transmitted pulses. Reduction of such wait times may be useful, for example, in multi-pulse acquisition sequences such as spin echo type acquisition sequences, wherein shorter times between echo pulses (shorter echo-spacing) may be achievable. In some embodiments, active Q-damping may be employed via circuits that are electrically coupled to receiving coil(s) in a surface probe. In some embodiments, active Q-damping may be employed via circuits that are inductively coupled to receiving coil(s) in a surface probe.

Some example surface-based NMR measurement methods may include deploying a surface-based NMR measurement apparatus or surface probe on or above the surface of the Earth or on an earthen engineered structure, such as a dam, levee, or backfilled area, such that the surface-based NMR measurement apparatus provides sensitivity at some depth or range of depths below the surface.

Properties detected or estimated may include, e.g., NMR properties, such as NMR signal amplitude or relaxation time distributions; hydrogeologic properties, such as moisture content, porosity, pore-size distributions, or permeability; and/or fluid properties, such as fluid composition or fluid diffusion. Properties may also be estimated that are relevant to geotechnical investigations or agricultural investigations, such as any of the aforementioned properties, clay content, bulk density, shear strength, saturation behavior, and/or drainage behavior.

Some example surface-based NMR measurement methods may include using at least one surface-based NMR measurement apparatus to perform a plurality of NMR measurements at a same location, wherein the radio frequencies used for the plurality of NMR measurements are varied to obtain measurements of the subsurface at different depths to obtain a depth profile of detected or estimated parameters. These methods may also include processing algorithms to enhance resolution of the detected or estimated properties as a function of depth.

Some example surface-based NMR measurement methods may include using at least one surface-based NMR measurement apparatus to perform a plurality of NMR measurements as the surface-based NMR measurement apparatus or surface probe coupled thereto is moved over different locations in a line, grid, or unstructured pattern to obtain measurements over a laterally extensive area. These measurements may be combined to obtain information about the 1D, 2D, and 3D variation in the parameters detected or estimated from the NMR measurements or to identify the locations of specific target subsurface features, such as a high moisture zones or high permeability zones.

Some example surface-based NMR measurement methods may include using at least one surface-based NMR measurement apparatus to perform a plurality of NMR measurements at a same location, wherein the measurements are separated in time. The plurality of NMR measurements may be used to detect a change over time of measured or estimated properties.

Some embodiments of surface-based NMR measurement apparatus and methods may utilize free induction decay (FID), spin echo, Carr-Purcell-Meiboom-Gill (CPMG), inversion recovery, saturation recovery or other specific NMR pulse sequences to accomplish the NMR measurements. In some embodiments, the NMR measurements may be performed in part to estimate the T1, T2 and/or T2* relaxation rates, fluid diffusion coefficients, and distributions thereof, of subsurface volume of interest.

In some embodiments, surface-based NMR measurement apparatus may include additional components to generate switchable gradients in the static magnetic field in subsurface volumes of interest. In some surface-based NMR measurement methods, switched gradient fields may be produced and used to enhance the spatial and/or temporal information of the NMR measurements.

FIG. 1 illustrates an example surface-based NMR measurement apparatus and locations of components thereof relative to the surface of the Earth, in accordance with various embodiments of this disclosure. Surface-based NMR measurement apparatus 100 is positionable at or above an Earth surface 140 and adapted perform NMR measurements of subsurface volume 141. NMR measurement apparatus 100 may be adapted perform NMR measurements at one or more depths below the surface 140 and within subsurface volume 141.

Surface-based NMR measurement apparatus 100 includes a housing 101 positionable at or above an Earth surface 140. Inside housing 101 are NMR spectrometer components 110 and surface probe 122. NMR spectrometer components 110 are inside a spectrometer housing 102, and include a controller 111, a signal generator 112, a power amplifier 113, a power supply 114, a matching means 115, a transmission line 118, an A/D converter 116, and a memory 117. Controller 111 is coupled with signal generator 112, signal generator 112 is coupled with power amplifier 113, and power amplifier 113 is coupled with power supply 114. Power amplifier 113 is also coupled with transmission line 118 via matching means 115. Memory 117 is coupled with A/D converter 116, and A/D converter 116 is also coupled with transmission line 118 via matching means 115. Transmission line 118 is coupled with surface probe 122 via matching means 121, wherein matching means 121 and surface probe 122 are outside the spectrometer housing 102 but inside the housing 101. Surface probe 122 may be positioned substantially at the bottom of housing 101, as shown.

The surface-based NMR measurement apparatus 100 may be placed on the surface 140 of the Earth or earthen structure to measure properties at one or more depths below the surface. It will be understood that the apparatus 100 may be placed "on" the surface 140 or otherwise near the surface 140, including just above the surface 140, e.g., by placing the apparatus on blocks or a raised platform. In some embodiments, the surface 140 may be in a pit or depression which may optionally be dug for apparatus 100. However, the apparatus 100 need not utilize components inserted below surface 140 into subsurface volume 141 for its operation.

Figure 2:
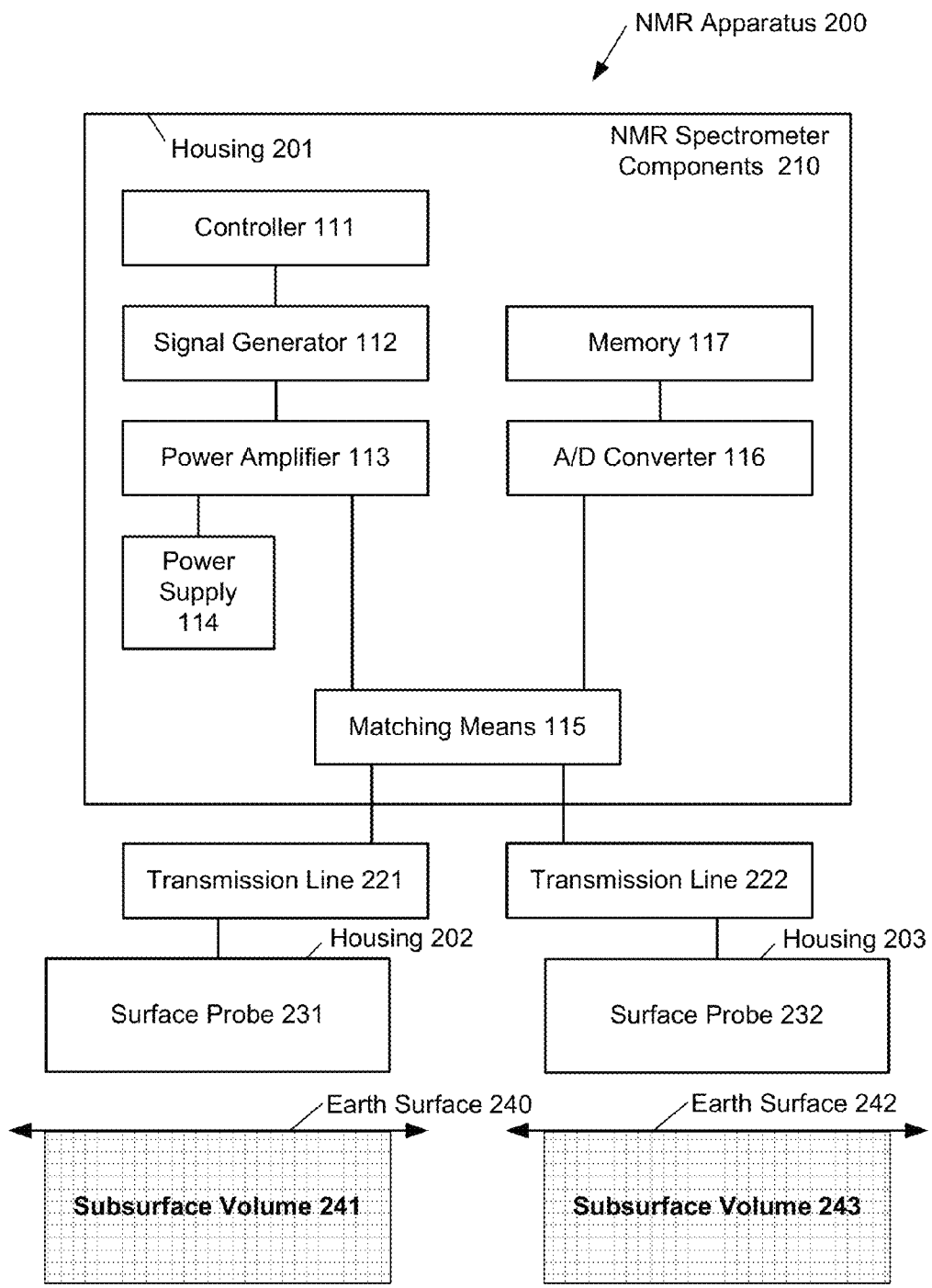
FIG. 2 illustrates an example surface-based NMR measurement apparatus with surface probes separated from NMR spectrometer electronics.

FIG. 2 illustrates an example surface-based NMR measurement apparatus 200 in which the spectrometer electronics 210 are separated from the surface probe(s) 231 and 232. NMR measurement apparatus 200 includes NMR spectrometer components 210 in a spectrometer housing 201. NMR spectrometer components 210 comprise controller 111, signal generator 112, power amplifier 113, power supply 114, matching means 115, an A/D converter 116, and a memory 117. Controller 111 is coupled with signal generator 112, signal generator 112 is coupled with power amplifier 113, and power amplifier 113 is coupled with power supply 114. Power amplifier 113 is also coupled with transmission lines 221 and 222 via matching means 115. Memory 117 is coupled with A/D converter 116, and A/D converter 116 is also coupled with transmission lines 221 and 222 via matching means 115. Transmission lines 221 and 222 are shown as coupled with NMR spectrometer components 210 external to spectrometer housing 201. Transmission lines 221 and 222 are coupled with surface probes 231 and 232, wherein surface probes 231 and 232 are also outside the spectrometer housing 201

Surface probes 231 and 232 may be positioned separately from spectrometer housing 201. Surface probes 231 and 232 may be positionable at or above Earth surfaces 240 and 242, respectively. Surface-based NMR measurement apparatus 200 may be adapted perform NMR measurements of multiple subsurface volumes 241 and 243 using surface probes 231 and 232. NMR measurement apparatus 200 may be adapted perform NMR measurements at one or more depths below the surfaces 240 and 242 and within subsurface volumes 241 and 243.

In some embodiments, surface-based NMR measurement apparatus 200 may comprise at least one additional electromagnetic field device adapted to measure electromagnetic noise. For example, surface probe 232 may be adapted to measure electromagnetic noise, rather than subsurface volume 243. When adapted to measure electromagnetic noise, a surface probe need not necessarily include all components of surface probes adapted for measuring subsurface volumes. For example, surface probes adapted for measuring electromagnetic noise need not necessarily include permanent magnets or transmit/receive switches. NMR spectrometer components 210 may comprise a memory configured to receive noise signals from surface probe 232, and NMR spectrometer components 210 may comprise a computer configured to reduce or cancel measured electromagnetic noise from detected NMR signals, e.g., to cancel electromagnetic noise measured by surface probe 232 from detected NMR signals measured by surface probe 231.

In FIG. 1 and FIG. 2, the illustrated NMR spectrometer components include a controller 111 such as a computer or digital processor which may be programmed to produce NMR pulse sequences appropriate and useful for performing NMR measurements in Earth formations. The controller 111 may also control other aspects of NMR measurement, such as by controlling switches. The controller 111 may also include human interface devices such as a keyboard and/or video monitor.

The controller 111 in the spectrometer electronics may be programmed to control digital and/or analog signal generator devices 112 which may produce appropriate low-voltage signals for generation of NMR pulse sequences. The power amplifier 113 may be configured to convert the low voltage NMR pulse sequence signals from the signal generating devices 112 into higher powered NMR pulse sequences. The output of the power amplifier 113 may generally comprise load-dependent electrical current and voltage waveforms, also referred to herein as radio frequency current waveforms.

In some embodiments, controller 111 may be configured to controllably adjust frequency of the radio-frequency pulses produced at surface probe 122. For example, controller 111 may be configured to accept an operator frequency input and to apply a frequency according to the operator frequency input. In some embodiments, controller 111 may be configured to accept an operator measurement depth input, and to apply a frequency according to the operator measurement depth input. In some embodiments, controller 111 may be configured to automatically apply different frequencies in a series of different NMR measurements, or in one or more pulses of a single NMR measurement.

Adjustment of the frequency may be operable to change the depth of the subsurface volume from which NMR signals are detected. Methods according to this disclosure may include activating NMR spectrometer components 110 to acquire at least two NMR measurements at different radio frequency electromagnetic pulse frequencies to measure subsurface volumes at different depths, e.g., sub-volumes of subsurface volume 141 at different depths. Recorded NMR signals from each of the NMR measurements may be used to determine at least one of the following example properties of the subsurface volumes: water content, porosity, soil moisture, T1, T2, permeability bound water content, mobile water content, fluid diffusion coefficient. Methods may include determining, for at least one of such example properties, the variation of the property as a function of depth.

In some embodiments, controller 111 may be adapted to produce NMR pulse sequences such as CPMG sequences in which a series of pulses are generated, separated by a duration ("echo-time") that may be on the order of 100 milliseconds or shorter. The echo-time spacing may be short (e.g. less than 1 millisecond) to optimize the signal to noise ratio and to reduce artifacts associated with molecular diffusion in fluids. Alternatively, the echo-time spacing may be made long or may be varied over a range of values in order to determine the diffusional properties of the subsurface fluids. CPMG sequences may be used to determine the T2 relaxation time distribution of the measured volume. In some embodiments, controller 111 may be adapted to employ other pulse sequences, such as saturation recovery experiments in which the "recovery-delay-time" is varied between measurements to determine the T1 relaxation time. The recovery time may be varied from values on the order of 1 millisecond or shorter to values of 5 seconds or longer. Multi-dimensional CPMG-based pulse sequences may also be used in which both the echo-time and or recovery time are varied between measurements to determine the covariance of T1, T2 and the fluid diffusion coefficient. Controller 111 may generally be adapted to conduct NMR measurement using pulse sequences, and optionally pulse sequence phase cycling, as described in U.S. Pat. Pub. US2012/0286779, entitled "SNMR PULSE SEQUENCE PHASE CYCLING", which is incorporated by reference herein.

Signal generator 112 may comprise a digital and/or analog output signal generator, which may be controlled by the controller 111, and which may produce low voltage NMR pulse sequence activating signals as input to the power amplifier 113. In some embodiments, signal generator 112 may be implemented by the controller 111 or by a separate signal generator device.

Power amplifier 113 may be configured to produce amplified NMR excitation waveforms as current and/or voltage waveforms. The power amplifier 113 may be configured to use signals produced by signal generator 112 and power from the power supply 114 to produce amplified signals for use by surface probes. Power supply 114 may comprise an appropriate power supply to power the power amplifier 113, the various other NMR spectrometer components, and optionally also the surface probes. Power supply 114 may be coupled to such other components to supply power as appropriate Receive electronics within NMR spectrometer components 110 and 210 may comprise A/D converter 116 and memory 117. A/D converter 116 may be configured to convert NMR response signals received from the surface probes 122, 231, and 232 from analog to digital form. Memory 117 may be configured to store digitized NMR response data. Memory 117 may comprise a memory in a computer, such as a computer implementing controller 111 or a separate computer. Digitized NMR response data may be processed and analyzed in a variety of useful ways. In some embodiments, a computer comprising memory 117 may also comprise software for processing and analysis of received NMR response data.

Matching means such as 115 and 121 may optionally be employed at one or both ends of transmission lines 118, 221, and 222. In some embodiments, matching means 115 and/or 121 may comprise impedance matching circuits configured to approximately match the load impedance of induction coil(s) in surface probes 122, 231, and 232, as seen through the transmission lines 118, 221, and 222, to the output impedance Zs of the power amplifier 113. Matching means 115 and 121 may include any matching means described in U.S. Pat. Pub. No. US2013/0187647, entitled "NMR LOGGING APPARATUS", which is incorporated by reference herein.

Example surface probe configurations for surface probes 122, 231, and 232 are described herein in connection with FIGS. 3-5 and FIGS. 9-11. In general, surface probes 122, 231, and 232 may include static magnetic field generating devices such as one or more permanent magnets or electromagnets. The static magnetic field generating devices may be configured so as to project a static magnetic field below the surfaces 140, 240 and 242, into subsurface volumes 141, 241, and 243. Different configurations and geometries of the static magnetic field generating devices may be preferred for different applications as described herein.

Surface probes 122, 231, and 232 may also include electromagnetic field devices such as one or more induction coils, antennae, or other magnetic or electric field emitting and measuring devices. Induction coils may be configured such that transmitting an electrical current through the induction coils produces radio frequency electromagnetic fields below the surfaces 140, 240 and 242, and within subsurface volumes 141, 241, and 243. NMR signals are activated when a volume of hydrogen in a static magnetic field B0 is exposed to a radio frequency magnetic field B1 that is tuned to the Larmor frequency of the static magnetic field B0, and the field B1 has a component which is perpendicular to the static magnetic field B0. Therefore, induction coils in surface probes 122, 231, and 232 may be configured to produce RF B1 fields below the Earth surfaces 140, 240 and 242, the RF B1 fields having a substantial component perpendicular to the static magnetic fields B0 produced by permanent magnets in the surface probes 122, 231, and 232. Different configurations and geometries of the induction coils may be preferred for different applications as described below. It is generally favorable to configure surface probes 122, 231, and 232 such that the RF magnetic fields produced by the induction coils are nominally perpendicular to the static magnetic fields generated by the permanent magnets.

Surface-based NMR measurement apparatus 200 may be configured to perform NMR measurements using one or more of the plurality of surface probes 231, 232. The NMR spectrometer components 210 may be configured to produce appropriate transmitted NMR pulse sequences, which may be routed to multiple individual surface probes to perform localized NMR measurements of different subsurface volumes 241, 243. In some embodiments, NMR spectrometer components 210 may be configured to perform NMR measurements with the plurality of surface probes 231, 232 over a common interval of time in which two or more of the surface probes 231, 232 are used.

Each surface probe 231, 232 may be connected to the NMR spectrometer components 210 via a transmission line or lines 221, 222, optionally using one or more of the impedance matching means described herein. Impedance matching means need not be employed on transmission lines in all embodiments. For example, impedance matching means need not be employed when transmission line length is suitably short. The impedance matching means 115 may be common to all surface probes 231, 232 and transmission lines 221, 222, or unique to each surface probe 231, 232 and transmission line 221, 222.

In some embodiments, NMR spectrometer components 210 may comprise a single NMR spectrometer components 210 unit. In some embodiments, a single NMR spectrometer components 210 unit may control one or more additional local NMR spectrometer components units, e.g., by connecting to a communications network. Network-enabled NMR spectrometer components 210 may also enable the NMR spectrometer components 210 and surface probes 231, 232 to operate autonomously, and/or from remote locations.

In some embodiments, methods for performing NMR measurements at the Earth's surface or on an earthen structure may comprise deploying a plurality of surface probes 231, 232 with associated transmission lines 221, 222 over a plurality of positions, and deploying a single NMR spectrometer components 210 unit or a number of NMR spectrometer components 210 units less than the number of deployed surface probes 231, 232 to perform NMR measurements in conjunction with the deployed surface probes 231, 232. In some embodiments, the NMR spectrometer components 210 unit or units may be programmed to perform multiple NMR measurements on multiple deployed surface probes 231, 232 over a common period of time. In some embodiments, the 231, 232 may be connected to a computer or communications network and monitoring and/or control of NMR measurements may be performed at least in part by human operators at locations remote from the NMR spectrometer components 210, such as inside a nearby building, or at a location many miles from the location of the NMR spectrometer components 210.

In some embodiments, one or more surface probes 231, 232 and transmission lines 221, 222 may be deployed and left in the same position for significant periods of time, such as weeks, months, or years, so as to enable repeated NMR measurements of the subsurface properties over intervals of time.

In some embodiments, long term NMR monitoring methods may be carried out using surface-based NMR measurement apparatus described herein. One or more surface probes 231, 232 and transmission lines 221, 222 may be left in place for extended periods of time, such as weeks, months, or years, and NMR spectrometer components 210 may be periodically or continuously attached to the one or more transmission lines 221, 222. NMR measurements may be performed by the surface-based NMR measurement apparatus 200 at various intervals throughout the extended period of time. Long term monitoring has important applications including the monitoring of subsurface contamination, monitoring the remediation of subsurface contamination including bioremediation, monitoring of changes in moisture content in the unsaturated zone, monitoring biogeochemical processes, monitoring carbon cycling, monitoring of formations subject to extraction of oil, gas, water or other commodities, and monitoring of formations subject to injection of carbon dioxide, water or other substances.

In some embodiments, NMR spectrometer components 210 may be deployed on surfaces within a mine, cave, underground structure, or other man made or natural cavity within the Earth. The NMR spectrometer components 210 may be deployed and operated within the subsurface cavity where surface probes 231, 232 may be deployed into one or more positions on the surface of the subsurface cavity.

Figure 3:
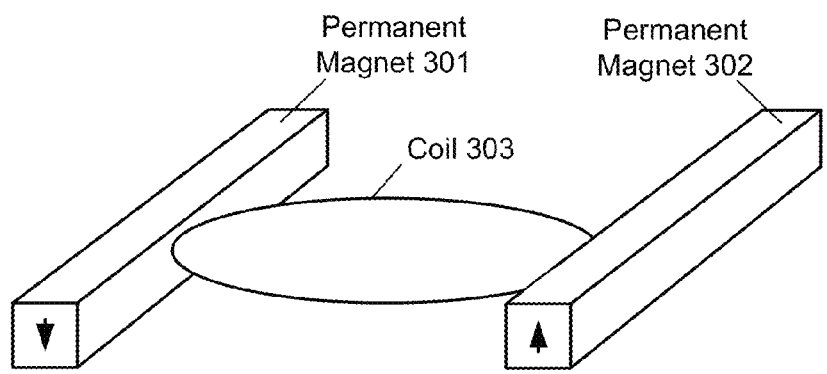
FIG. 3 illustrates an example surface probe configuration including permanent magnets and an induction coil.

FIG. 3 illustrates an example surface probe configuration including permanent magnets and an induction coil. An induction coil measurement antenna 303 is positioned between two long permanent magnets 301 and 302 with opposite vertical polarity, as indicated by arrows on the permanent magnets 301 and 302. The induction coil 303 is shown as a circle, but may also be a square, rectangle, oval, or other closed loop shape.

Figure 4:
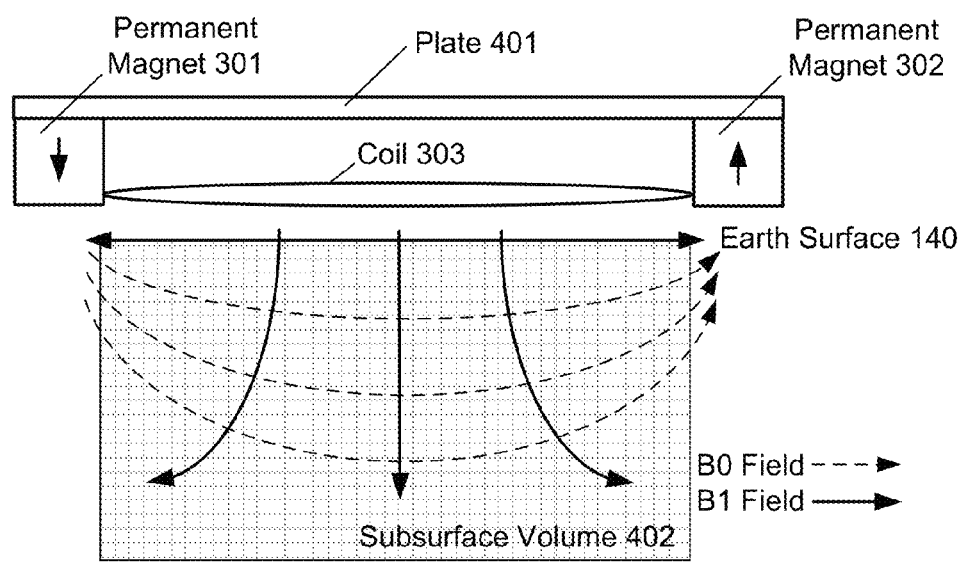
FIG. 4 illustrates an example surface probe configuration including permanent magnets, an induction coil, and a metallic plate.

FIG. 4 illustrates an example surface probe configuration including permanent magnets, an induction coil, and a metallic plate. Induction coil measurement antenna 303 is positioned between permanent magnets 301 and 302 with opposite vertical polarity, as shown in FIG. 3. A metallic plate 401 is placed across permanent magnets 301 and 302. Plate 401 may be made from iron or iron alloys as appropriate. Plate 401 may focus the static magnetic field B0 produced by permanent magnets 301 and 302. In some embodiments, plate 401 may also serve as a yoke to physically join the permanent magnets 301 and 302.

FIG. 4 also illustrates Earth surface 140, subsurface volume 402, static magnetic field B0 and radio frequency magnetic field B1. The illustrated geometry produces vertical B1 fields that are nominally perpendicular to the horizontal B0 static magnetic field. Here the plane of the induction coil 303 is substantially parallel with the surface 140, and the plane of the induction coil 303 is substantially parallel with the orientation of the static magnetic field B0 at the center of the induction coil 303.

Figure 5:
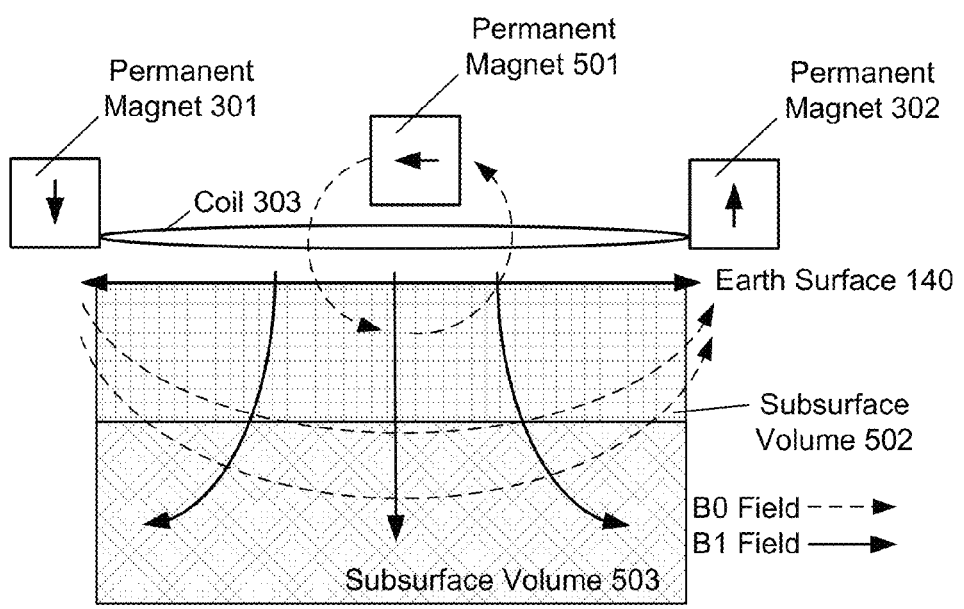
FIG. 5 illustrates an example surface probe configuration including permanent magnets with vertical and horizontal polarizations and an induction coil.

FIG. 5 illustrates an example surface probe configuration including permanent magnets with vertical and horizontal polarizations and an induction coil. Induction coil measurement antenna 303 is positioned between permanent magnets 301 and 302 with opposite vertical polarity, as shown in FIG. 3. A third magnet 501 with horizontal polarization is added to the middle of the magnet array, serving to increase the horizontal component of the static field B0 at the center of the array. This configuration may employ similar structure to magnet arrays known in the art as "sparse Halbach" arrays. Additional magnets may be added to the array to increase the static magnetic field amplitude, or to increase the volume over which B0 fields are nominally perpendicular to the B1 fields. Here again the plane of the induction coil 303 is substantially parallel with the orientation of the static magnetic field at the center of the induction coil 303, and the plane of the induction coil 303 is also substantially parallel with the surface 140.

FIG. 5 also illustrates Earth surface 140, subsurface volume 502 extending through a first depth below surface 140, and subsurface volume 503 extending from the bottom of subsurface volume 502 through a second depth below surface 140. Subsurface volumes 502 and 503 may comprise very shallow subsurface volumes at different depths. For example, subsurface volume 502 may comprise a very shallow subsurface volume from 0-2 feet deep, and subsurface volume 503 may comprise a very shallow subsurface volume from 2-4 feet deep. Static magnetic field B0 and radio frequency magnetic field B1 may differ in strength and direction in the different subsurface volumes 502 and 503. NMR spectrometer components may be adapted to accommodate such differences when performing NMR measurements of the different subsurface volumes 502, 503, or 502 and 503 combined.

Figure 6:
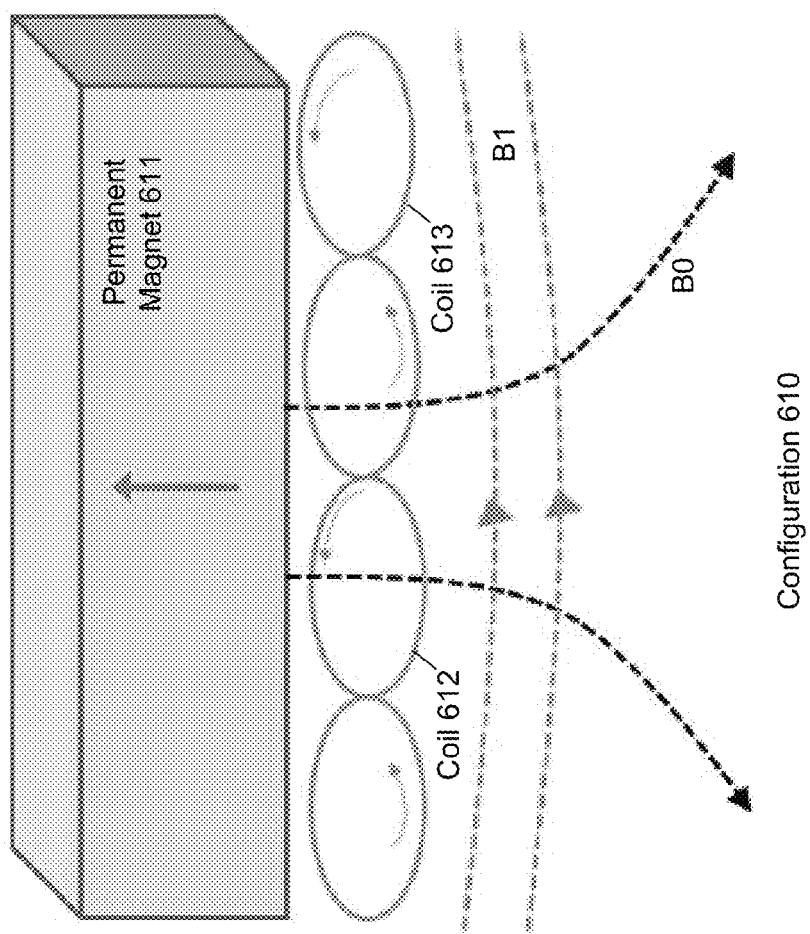
FIG. 6 illustrates example geometric configurations for permanent magnets and induction coils within a surface probe.
Figure 6:
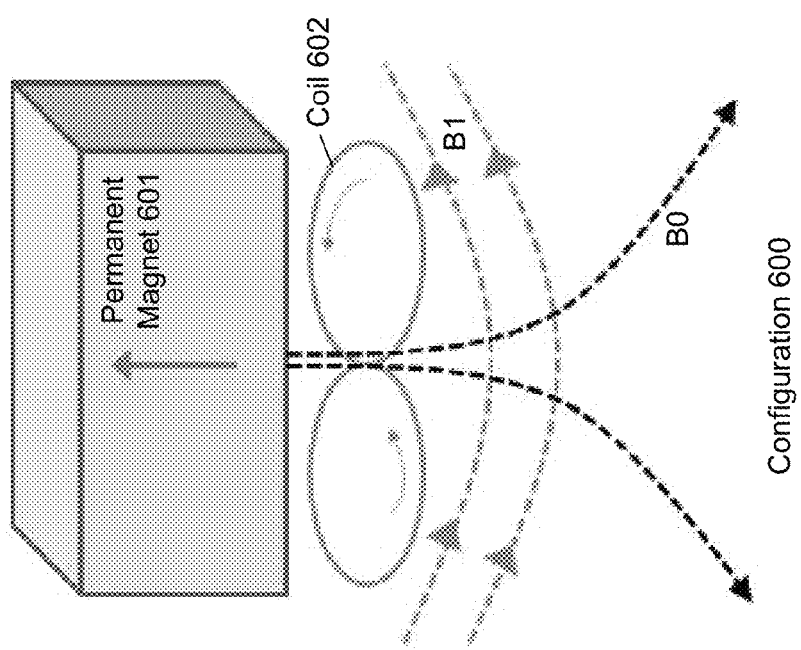

FIG. 6 illustrates example geometric configurations 600 and 610 for permanent magnets and induction coils within a surface probe. Example configuration 600 includes a figure-eight shaped induction coil 602 and a permanent magnet 601 with substantially uniform vertical polarity. The plane of the induction coil 602 is substantially perpendicular to the orientation of the static magnetic field B0 produced by the permanent magnet 601 at the center of the figure-eight. Figure-eight induction coil 602 may comprise two closed loops connected and wound in opposite directions (i.e. one clockwise, one counter-clockwise). The figure-eight loop geometry produces B1 fields that are substantially parallel to the plane of the figure-eight induction coil 602. The illustrated configuration of the permanent magnet 601 with uniform vertical polarity produces a static magnetic field B0 that is substantially perpendicular to the plane of the induction coil 602. Thus, the condition of B1 substantially perpendicular to B0 is met. One advantage of the figure-eight geometry of induction coil 602 is that it automatically suppresses interfering noise that may come from external radio frequency magnetic field sources.

Example configuration 610 includes two figure-eight shaped induction coils 612 and 613 and a permanent magnet 611 with substantially uniform vertical polarity. Additional induction coils may be included as appropriate for particular embodiments. As with configuration 600, the plane of the induction coils 612 and 613 is substantially perpendicular to the orientation of the static magnetic field B0 produced by the permanent magnet 611 at the center of the combined figure-eight induction coils 612 and 613. Figure-eight induction coils 612 and 613 may comprise two closed loops connected and wound in opposite directions (i.e. one clockwise, one counter-clockwise). The figure-eight loop geometry produces B1 fields that are substantially perpendicular to the plane of the figure-eight induction coils 612 and 613. The illustrated configuration of the permanent magnet 611 with uniform vertical polarity produces a static magnetic field B0 that is substantially vertical to the plane of the induction coils 612 and 613. Thus in configuration 610 the condition of B1 substantially perpendicular to B0 is also met.

Many other geometric configurations of permanent magnet(s) and induction coil(s) may be constructed that will satisfy the general parameter of B1 perpendicular to B0. Further, some surface-based NMR measurement apparatus may include multiple induction coils and/or multiple permanent magnets configured with different geometries, where different combinations of induction coils and permanent magnets may be used for different purposes, for example, to measure different subsurface volumes or to reduce sensitivity to external radio frequency magnetic field sources.

In some embodiments, surface-based NMR measurement apparatus may be configured to take advantage of gradient based imaging to sample specific volumes within the subsurface. The basis of gradient based imaging is that the NMR signal may be activated when the frequency of the transmitted radio frequency B1 field matches the Larmor frequency for the static B0 field at a certain position. A static field source such as a magnet may produce a static magnetic field B0 that has a gradient moving away from the magnet. Close to the magnet, the B0 field is strong and the field strength decreases with the distance from the static magnetic field source. Thus the frequency at which the NMR signal may be activated decreases with distance from the magnet. For a magnet or magnet array deployed on the surface of the Earth, the frequency decreases as a function of depth.

Thus, in some embodiments, surface-based NMR measurement apparatus may be tuned to specific frequencies in order to isolate NMR measurements to a specific region of the subsurface. In the aforementioned magnet and induction coil geometries, the gradient of the B0 field is in the depth direction. Thus, by tuning the system to lower frequencies, the measurement volume may be moved to greater depths. By tuning to higher frequencies, the measurement volume may be moved to shallower depths.

Figure 7:
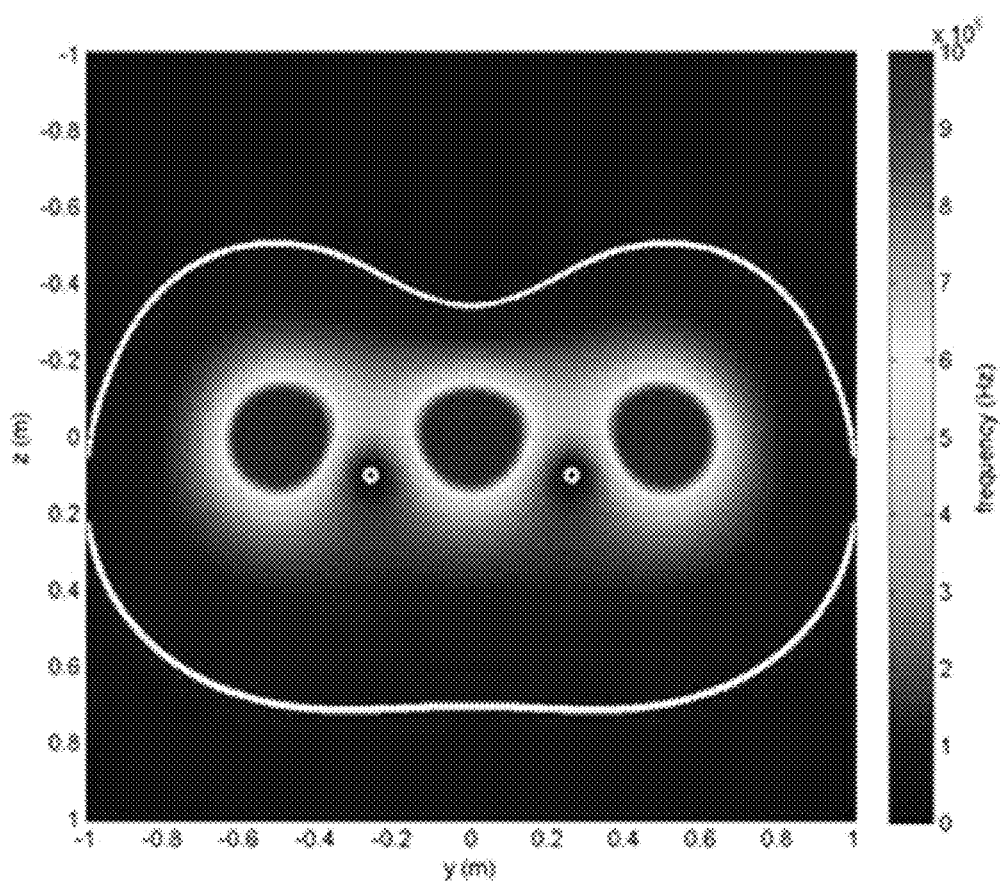
FIG. 7 illustrates spatial contours of a measurement volume for a measurement frequency range providing sensitivity at a particular profiling depth.

FIG. 7 illustrates spatial contours of a measurement volume for a measurement frequency range providing sensitivity at a particular profiling depth. Larmor frequency varies as a function of the static magnetic field strength. FIG. 7 illustrates the case of a sparse Halbach magnet array comprising three magnets (static magnetic field generating devices) such as illustrated in FIG. 5, wherein a cross-section perpendicular long axis of the magnets is shown. The zone covered by the outer white line indicates the zone activated by a transmitted B1 tuned to a frequency of 40 kHz with a bandwidth of 500 Hz. By increasing or decreasing the measurement frequency, the zone may be moved up or down. As illustrated in FIG. 7, the zone is larger on one side of the magnets (under the magnets) than it is on the opposite side of the magnets (above the magnets), due to a larger magnetic field under the magnets than above the magnets. In an arrangement such as illustrated in FIG. 5, the larger magnetic field, illustrated under the magnets in FIG. 7, is at one side (under) the example surface probe illustrated in FIG. 5, while the smaller magnetic field, illustrated above the magnets in FIG. 7, is at an opposite side (above) the example surface probe illustrated in FIG. 5.

Figure 8:
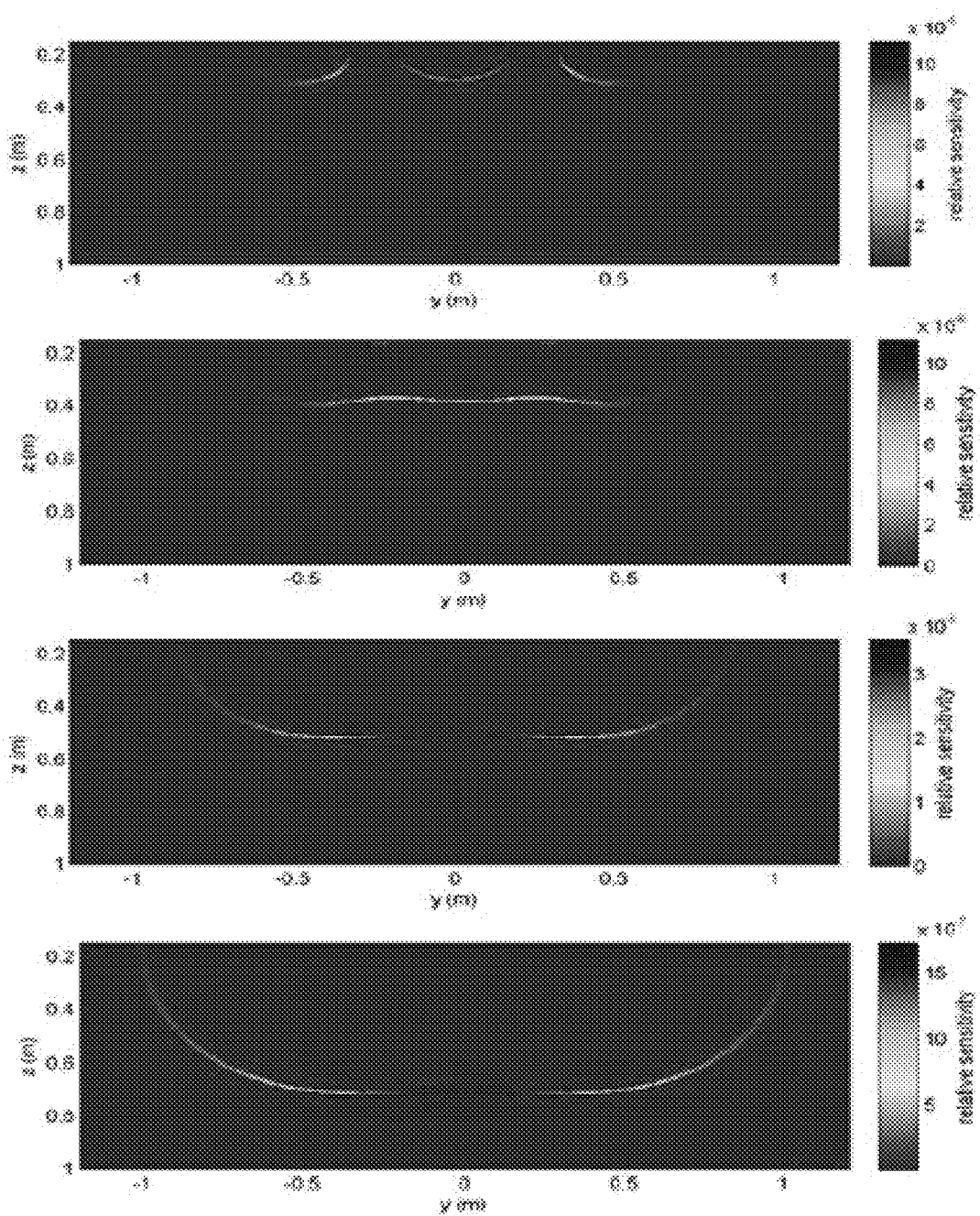
FIG. 8 illustrates variation in the depth of the measurement volume and sensitivity pattern for four different measurement frequencies.

FIG. 8 illustrates variation in the depth of the measurement volume and sensitivity pattern for four different measurement frequencies. FIG. 8 shows the relative sensitivity to different volumes of the subsurface for measurements at four different frequencies, decreasing from top down. It can be seen that for measurements at higher frequencies, the sensitive zone is located close to the surface where the magnets are positioned; as the frequency is decreased the sensitive zone moves to greater depths. Thus by tuning the measurement to different frequencies, NMR measurements can be obtained for different depths within the subsurface and a complete profile of properties may be obtained. These properties may include moisture content, porosity, pore size distribution, or any other property available from the NMR measurement.

In some embodiments, measurement frequencies applied by surface-based NMR measurement apparatus and methods disclosed herein may range from 10 kHz to 100 MHz. In embodiments generally applicable to measurement of very shallow subsurface volumes, measurement frequencies applied by surface-based NMR measurement apparatus and methods disclosed herein may range from 40 kHz to 5 MHz. Higher frequencies within a given range of frequencies generally provide sensitivity close to the static magnetic field source (i.e. shallower). Several advantages of measurements at high frequencies include high signal-to-noise, strong magnetic field gradients for sensitivity to fluid diffusion, reduced coil ringing, and the ability to use shorter pulses. Lower frequencies provide sensitivity further from the magnetic field source (i.e. deeper). Advantages of measurements at low frequency include low magnetic field gradients for sensitivity to surface relaxation and pore geometry, as well as reduced internal field gradients associated with magnetic soils.

In some embodiments, measurements may be repeated and the resulting data from multiple measurements may be averaged or "stacked" to increase the signal-to-noise ratio. In some instances, it may be desirable to wait a time longer than T1 between repeated measurements at a given frequency such that the fluid NMR state within the sampled volume is allowed to recover to equilibrium before the measurement is repeated. In some embodiments, measurements at one or more other frequencies may be made during wait times while the NMR processes at an earlier measured frequency are allowed to recover.

In some embodiments, phase cycling procedures may be used to reduce measurement artifacts such as coil ringing or switching artifacts, as well as undesired NMR artifacts such as FID signals following refocusing pulses. Example phase cycling techniques are described in U.S. Pat. Pub. US2012/0286779, entitled "SNMR PULSE SEQUENCE PHASE CYCLING", which is incorporated by reference herein.

Figure 9:
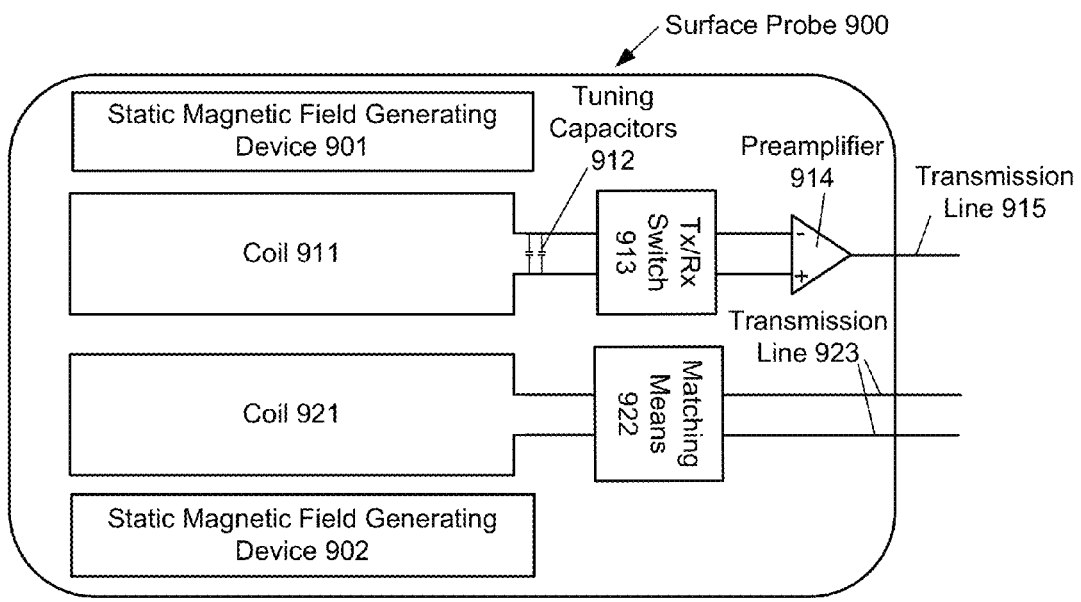
FIG. 9 illustrates an example surface probe including separate transmitting and receiving coil.

FIG. 9 illustrates an example surface probe including separate transmitting and receiving coils. FIG. 9 illustrates a top view of example surface probe 900. Surface probe 900 comprises static magnetic field generating devices 901 and 902, and an array of induction coils including induction coil 911 and induction coil 921. Induction coil 921 is configured as a transmit coil, and induction coil 911 is configured as a receive coil. Induction coil 921 is coupled with matching means 922 and transmission line 923. Induction coil 911 is coupled with tuning capacitors 912, transmit/receive switch 913, preamplifier 914, and a second transmission line 915.

Figure 10:
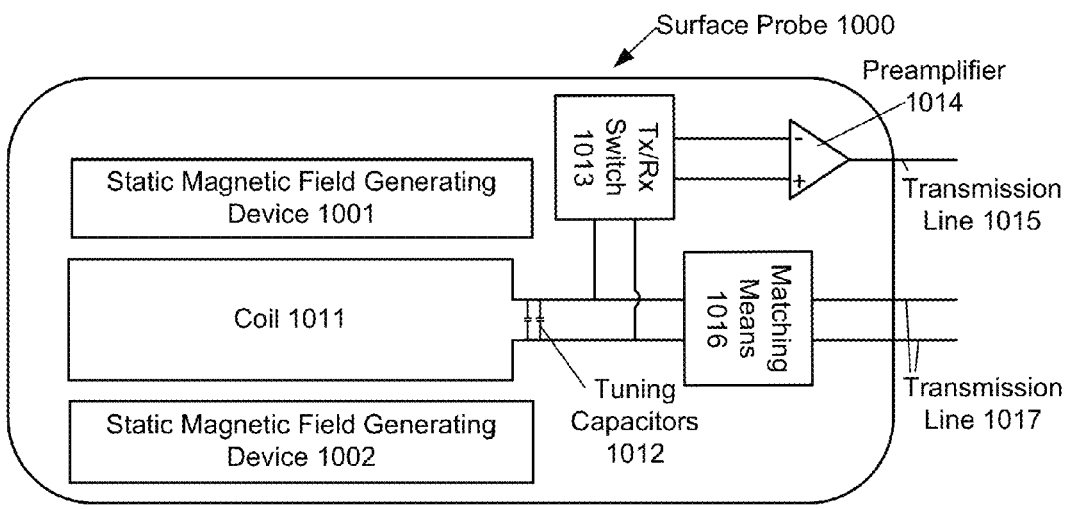
FIG. 10 illustrates an example surface probe including a combination transmitting/receiving coil.

FIG. 10 illustrates an example surface probe including a combination transmitting/receiving coil. FIG. 10 illustrates a top view of example surface probe 1000. Surface probe 1000 comprises static magnetic field generating devices 1001 and 1002, and an array of induction coils including combination transmitting/receiving induction coil 1011. Induction coil 1011 is coupled with tuning capacitors 1012, transmit/receive switch 1013, and matching means 1016. Matching means 1016 is coupled with transmission line 1017. Transmit/receive switch 1013 is coupled with preamplifier 1014, and preamplifier 1014 is coupled with a second transmission line 1015.

Figure 11:
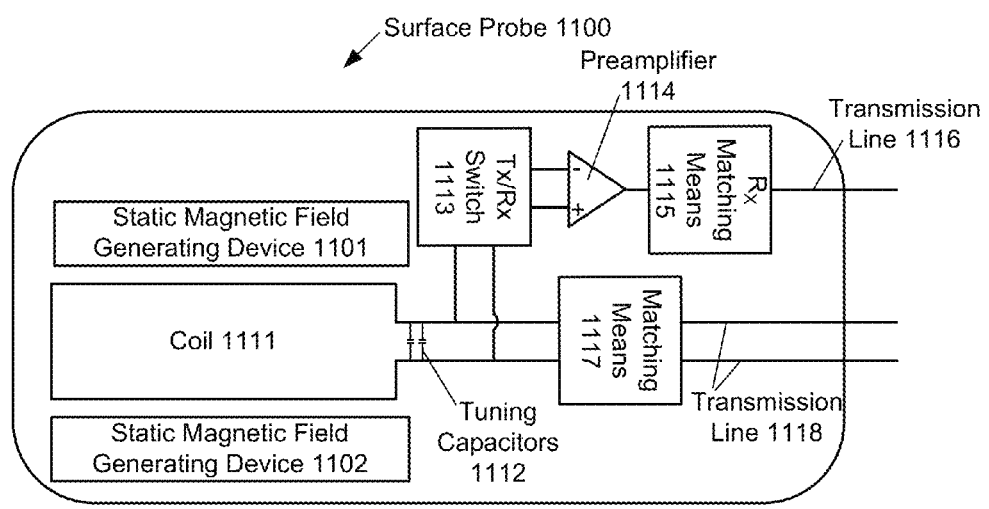
FIG. 11 illustrates an example surface probe including transmit and receive matching means.

FIG. 11 illustrates an example surface probe including transmit and receive matching means. FIG. 11 illustrates a top view of example surface probe 1100. Surface probe 1100 comprises static magnetic field generating devices 1101 and 1102, and an array of induction coils including combination transmitting/receiving induction coil 1111. Induction coil 1111 is coupled with tuning capacitors 1112, transmit/receive switch 1113, and matching means 1017. Matching means 1017 is coupled with transmission line 1118. Transmit/receive switch 1113 is coupled with preamplifier 1114, preamplifier 1014 is coupled with receive matching means 1015, and receive matching means 1015 is coupled with a second transmission line 1016.

Alternative embodiments according to FIGS. 9-11 may include different numbers of induction coils and/or static magnetic field generating devices. For example surface probe 1000 may omit static magnetic field generating device 1002, leaving one static magnetic field generating device 1001, e.g., as illustrated in configurations 600 and 610 in FIG. 6, or may add a static magnetic field generating device, e.g., to form a sparse Halbach array as shown in FIG. 5. Surface probe 1000 may also add electromagnetic field devices, such as additional induction coils, e.g., by including multiple FIG. 8 loops as illustrated in configuration 610 in FIG. 6.

In general, surface probes according to FIGS. 9-11 may include many aspects of borehole probes such as described in U.S. Pat. Pub. No. US2013/0187647, entitled "NMR LOGGING APPARATUS", which is incorporated by reference herein.

In some embodiments, tuning may be accomplished through the use of tuning capacitors 912, 1012, 1112 connected to the induction coils. In some embodiments, surface-based NMR measurement apparatus may be tuned in transmit mode or tuned in both transmit and receive mode. Tuning the apparatus in transmit mode may be included to maximize the power transfer between power amplifier and the induction coils. Tuning the apparatus in receive mode may increase the amplitude of the received NMR signal detected on the induction coils.

In some embodiments, the tuning may be configured to be adjustable so as to maximize power transfer and detection when the measurement frequency is adjusted. In some embodiments, the configuration of adjustable tuning may be accomplished using additional tuning capacitors that may be switched in or out of circuit to adjust the total tuning capacitance in the circuit. In other embodiments the configuration of controllable tuning may be accomplished using additional coil turns that may be switched in or out of circuit with the induction coil to allow a controllable tuning inductance in the circuit.

The induction coils in surface probes 900, 1000, 1100 may be configured to generate radio frequency magnetic fields during a transmit mode to cause precession of NMR active nuclei, and to detect the resulting magnetic fields generated by the NMR processes during a receive mode. Transmitting and receiving functions may be accomplished by a same induction coil, e.g., in arrangements such as FIGS. 10 and 11, or by separate transmitting and receiving induction coils, e.g., as shown in FIG. 9.

Induction coils may comprise single turn or multiple turn induction loops, also referred to herein as current loops and/or coils. In some embodiments, surface probes 900, 1000, 1100 may include, in place of the illustrated induction coils, partial coaxial type antennae, or any other type of antenna or induction coil suitable for generating radio frequency magnetic fields in an Earth formation and for detecting NMR responses from the Earth formation. In some embodiments, a transmitting induction coil and a receiving induction coil may be inductively coupled with a non-zero mutual inductance during a transmit mode, as described further herein.

Surface probes 900, 1000, 1100 may include a transmit/receive switches 913, 1013, 1113 to isolate receive electronics such as the preamplifiers 914, 1014, 1114 and other receive electronics that may be coupled therewith, from high voltage on the receiving coils during transmit mode, and to couple the receiving coils to receive electronics during receive mode. The transmit/receive switches 913, 1013, 1113 may also reduce noise from the transmitting circuitry from interfering with detection of NMR signals in receive mode. Any functional embodiment may be used for the transmit/receive switches 913, 1013, 1113. For example in some embodiments, the switches 913, 1013, 1113 may be actively controlled relays. In another embodiment the switches 913, 1013, 1113 may be comprised of crossed diodes which passively isolate the receive electronics by shorting high voltages before the receive electronics inputs.

In some embodiments, surface probes 900, 1000, 1100 may include preamplifiers 914, 1014, 1114 to amplify detected NMR signals to suitable levels for digitization and/or for analog transmission to NMR spectrometer components. The transmit/receive switches 913, 1013, 1113 and preamplifiers 914, 1014, 1114 are example means for detecting NMR signals induced in induction coils in surface probes 900, 1000, 1100. In some embodiments, an output impedance of the preamplifiers 914, 1014, 1114 may be matched to a characteristic impedance of second transmission lines 915, 1015, 1116.

In some embodiments, surface probes 900, 1000, 1100 may comprise means for coupling transmission lines with induction coils. For example, an electrical interface may be configured to connect and disconnect transmission lines from the surface probes 900, 1000, 1100, so the components can be separated for transport and storage.

In some embodiments, surface probes 900, 1000, 1100 may include a means (not shown) for reducing the Q-factor of the transmitting and/or receiving antennae. This Q-damping means may comprise passive electronics and/or actively controlled electronics circuits. The Q-damping electronics circuits may be electrically connected to one or more of the receiving antenna, for example as described in U.S. Pat. No. 5,055,788, which is incorporated by reference herein, or inductively coupled to one or more of the transmitting and/or receiving antennae as described in U.S. Pat. No. 6,291,994, which is incorporated by reference herein. The Q-damping means may be active during either all or part of the transmit mode, during all or part of the receive mode, or during part or all of both modes. Passive Q-damping circuits may include diode-based circuits that increase effective circuit resistance when a transmitting voltage exceeds a diode turn-on voltage. Actively controlled Q-damping circuits may be controlled via external timing from a surface-based controller, such as controller, or automatically triggered from the timing of a transmitted pulse sequence.

In some embodiments, transmitting induction coils 921, 1011, 1111 within the surface probes 900, 1000, 1100 may be electrically connected to transmission lines 923, 1017, 1018, which may be coupled to power amplifier 1113 in NMR spectrometer components. Radio frequency current waveforms may be generated by the power amplifier 113 and transferred by the transmission lines 923, 1017, 1018 to the induction coils 921, 1011, 1111 in the surface probes 900, 1000, 1100, which may convert the electrical energy from the power amplifier 113 into local Alternating Current (AC) magnetic fields which activate NMR processes in the subsurface volumes. One or more matching means 922, 1016, 1117 may be employed so as to approximately match the output impedance of the power amplifier 113 to the input impedance of the transmitting induction coils 921, 1011, 1111.

The receiving induction coils 911, 1011, 1111 within the surface probes 900, 1000, 1100 may be electrically connected to receive electronics within the surface probes 900, 1000, 1100, such as the preamplifiers 914, 1014, 1114. One or more A/D converters such as 116, located either within the surface probe or in the NMR spectrometer components, may be used to sample and store detected and preamplified NMR signals.

Figure 12:
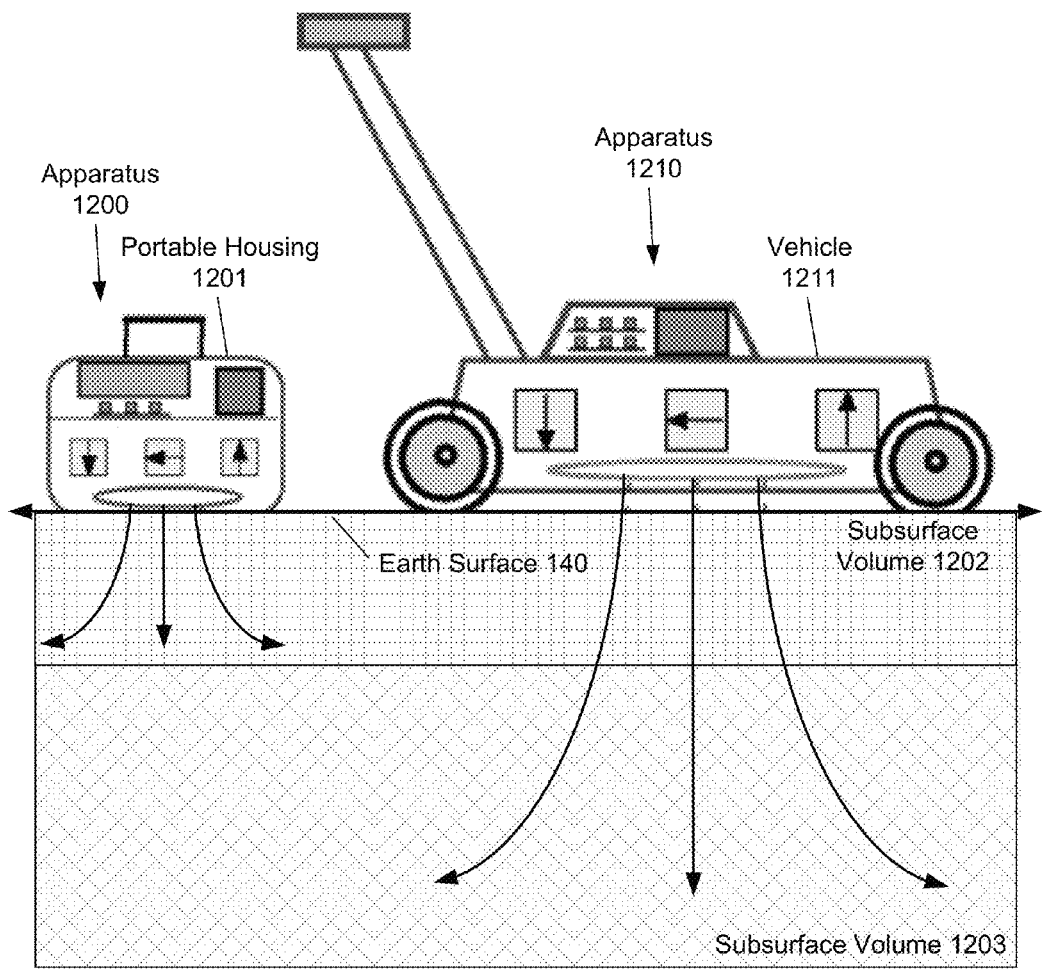
FIG. 12 illustrates two example surface-based NMR measurement apparatus configured for easy portability.

FIG. 12 illustrates two example surface-based NMR measurement apparatus configured for easy portability. Surface-based NMR measurement apparatus 1200 is arranged within a portable housing 1201. Surface-based NMR measurement apparatus 1210 is arranged within a vehicle 1211. Surface-based NMR measurement apparatus 1200 and 1210 may be arranged so that the surface probe(s) are positioned substantially at a bottom of the portable housing 1201 or vehicle 1211. Portable housing 1201 and vehicle 1211 are positionable at or above Earth surface 140 and may be configured to perform NMR measurements of subsurface volumes 1202, 1203, and/or 122 and 1203 combined, wherein subsurface volume 1202 may comprise, e.g., a very shallow subsurface volume and subsurface volume 1202 and 1203 combined may comprise a shallow subsurface volume.

Surface-based NMR measurement apparatus 1200 and 1210 may be configured for easy portability by placing NMR spectrometer components and surface probes within a same primary housing. In some embodiments, as shown at left, the substantially entire apparatus may be contained in a hand portable box which may be lifted and positioned in a desired measurement location. In other embodiments, as shown at right, the primary housing may be configured with wheels or sleds, or in a special purpose motorized vehicle for easy portability without requiring lifting. A human interface device, such as a video screen, keypad, and/or touch-screen may be incorporated so that a human user can operate the apparatus 1200, 1210 and obtain real-time information from the measurements when using the apparatus 1200, 1210.

In some embodiments the apparatus 1200, 1210 may be used to collect a measurement at a single location or a plurality of locations. For measurements collected at a plurality of locations the measurements may be combined to form a two-dimensional or three-dimensional map of the parameters estimated from the recorded and processed NMR data. Measurements may also be collected at a plurality of locations in order to determine the location of a specific target or feature, such as a high permeability zone or high moisture zone. In some embodiments the apparatus 1200, 1210 may be moved while activating the NMR spectrometer components multiple times to make multiple surface-based NMR measurements of multiple subsurface volumes as the portable housing 1201 or vehicle 1211 moves.

In some embodiments the apparatus may be used primarily to detect the presence of subsurface fluids or further may be used to characterize the properties of the fluids or fluid-bearing formations. The apparatus may be used for a wide range of characterization purposes such as geotechnical evaluations and agricultural evaluations.

In some embodiments of methods for geotechnical investigations, the NMR apparatus disclosed herein may be deployed on an Earth formation or an engineered earthen formation, such as a dam, levee, or backfilled area. Parameters of geotechnical relevance may be estimated from the measured NMR data. Such geotechnical properties may include soil moisture, pore size, clay content, shear strength, and compressibility. The apparatus may further serve all functions to replace the use of neutron measurement devices, widely applied in geotechnical investigations, for determining water content.

In some embodiments of methods for agricultural applications, the NMR apparatus disclosed herein may be used in an agricultural field. In some embodiments the apparatus may be used to locate zones of high water content prior to planting in order to identify zones of poor drainage. In some embodiments the apparatus may be used following planting to determine whether irrigated water is infiltrating below the root zone and the information may be used to adjust irrigation strategies.

In some embodiments, measurements may be repeated in time to estimate parameters that are not directly available from a single NMR measurement. For example, the moisture content profile may be measured at a single location over time and combined to determine infiltration or evapotranspiration rates. As another example, a moisture content profile may be measured at a position before freezing winter conditions and after freezing winter conditions to determine the volume of frozen water within a soil layer.

Other embodiments of the methods may include any NMR-based characterization of the shallow or very shallow subsurface that may be obtained through the use of surface-based NMR measurement apparatus disclosed herein.

There are various approaches by which apparatus and methods processes described herein can be implemented (e.g., hardware, software, and/or firmware), and the preferred approach may vary with the context in which the apparatus and methods are deployed. For example, if an implementer determines that speed and accuracy are paramount for operations of a computer or controller, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various embodiments have been disclosed herein, other aspects and embodiments will be apparent to those skilled in art.

The invention claimed is:

1. A surface-based Nuclear Magnetic Resonance (NMR) measurement apparatus, comprising:
one or more surface probes positionable at or above a surface of the Earth, at least one of the surface probes comprising:
three or more static magnetic field generating devices arranged so as to generate a static magnetic field in a subsurface volume, wherein the static magnetic field is larger at one side of the at least one surface probe than at an opposite side of the at least one surface probe; and
one or more electromagnetic field devices arranged to transmit radio frequency electromagnetic pulses to cause a precession of NMR spins within the subsurface volume, and arranged to detect NMR signals produced by the precession of NMR spins in the static magnetic field in the subsurface volume; and
NMR spectrometer components connected to the one or more electromagnetic field devices and configured to control the radio frequency electromagnetic pulses and to record detected NMR signals from the subsurface volume.

2. The surface-based NMR measurement apparatus of claim 1, wherein the three or more static magnetic field generating devices comprises a permanent magnet array.

3. The surface-based NMR measurement apparatus of claim 2, wherein the permanent magnet array comprises two or more permanent magnets with polarity directed in a single direction.

4. The surface-based NMR measurement apparatus of claim 2, wherein the permanent magnet array comprises two or more permanent magnets with polarity directed in different directions.

5. The surface-based NMR measurement apparatus of claim 2, wherein the permanent magnet array comprises a sparse Halbach array.

6. The surface-based NMR measurement apparatus of claim 1, wherein the at least one surface probe further comprises a metallic plate positioned between static magnetic field generating devices and parallel to the surface of the Earth when the at least one surface probe is positioned on the surface of the Earth, wherein the metallic plate focuses the static magnetic field in the subsurface volume.

7. The surface-based NMR measurement apparatus of claim 1, wherein the one or more electromagnetic field devices comprises at least one induction coil.

8. The surface-based NMR measurement apparatus of claim 7, wherein the at least one induction coil is arranged in a figure-eight geometry.

9. The surface-based NMR measurement apparatus of claim 1, wherein the three or more static magnetic field generating devices and the one or more electromagnetic field devices are arranged within the at least one surface probe so that when the at least one surface probe is positioned at or above the surface of the Earth, the radio frequency electromagnetic fields transmitted from the one or more electromagnetic field devices exhibit a component that is perpendicular to the static magnetic field within the subsurface volume.

10. The surface-based NMR measurement apparatus of claim 1, wherein the subsurface volume is a very shallow subsurface volume.

11. The surface-based NMR measurement apparatus of claim 1, wherein the surface of the Earth comprises a surface of a man-made structure.

12. The surface-based NMR measurement apparatus of claim 1, wherein the at least one surface probe comprises a transmit/receive switch adapted to isolate NMR spectrometer components for recording the detected NMR signals during transmission of the radio frequency electromagnetic pulses.

13. The surface-based NMR measurement apparatus of claim 1, wherein the at least one surface probe and the NMR spectrometer components are adapted within a portable housing or a vehicle, and wherein the at least one surface probe is positioned at a bottom of the portable housing or the vehicle.

14. The surface-based NMR measurement apparatus of claim 1, wherein the NMR spectrometer components comprise at least a controller, a signal generator, a power amplifier, a power supply, an Analogue to Digital (A/D) converter, and a memory adapted to record detected NMR signals.

15. The surface-based NMR measurement apparatus of claim 1, further comprising at least one additional electromagnetic field device adapted to measure electromagnetic noise, and wherein the NMR spectrometer components comprise a computer configured to reduce or cancel measured electromagnetic noise from detected NMR signals.

16. The surface-based NMR measurement apparatus of claim 1, wherein the NMR spectrometer components are configured to controllably adjust a frequency of the radio frequency electromagnetic pulses.

17. The surface-based NMR measurement apparatus of claim 16, wherein adjustment of the frequency changes a depth of the subsurface volume.

18. The surface-based NMR measurement apparatus of claim 1, wherein the one side of the at least one surface probe comprising a larger static magnetic field is an underside of the at least one surface probe, and wherein the opposite side of the at least one surface probe is over the at least one surface probe.

19. The surface-based NMR measurement apparatus of claim 1, wherein the subsurface volume is a shallow subsurface volume.

20. A surface-based Nuclear Magnetic Resonance (NMR) measurement method, comprising:
  positioning at least one surface probe at or above a surface of the Earth, over a subsurface volume of interest, the at least one surface probe comprising:
    three or more static magnetic field generating devices arranged so as to generate a static magnetic field in the subsurface volume, wherein the static magnetic field is larger at one side of the at least one surface probe than at an opposite side of the at least one surface probe; and
    one or more electromagnetic field devices arranged to transmit radio frequency electromagnetic pulses, and arranged to detect NMR signals; and
  activating NMR spectrometer components connected to the one or more electromagnetic field devices to transmit the radio frequency electromagnetic pulses into the subsurface volume to cause a precession of NMR spins within the subsurface volume; and
  recording, with the NMR spectrometer components, NMR signals produced by the precession of NMR spins in the static magnetic field in the subsurface volume.

21. The surface-based NMR measurement method of claim 20, wherein the three or more static magnetic field generating devices comprise a permanent magnet array, and wherein the one or more electromagnetic field devices comprises at least one induction coil arranged within the at least one surface probe so that when the at least one surface probe is positioned at or above the surface of the Earth, the at least one induction coil defines a plane parallel to the surface of the Earth and parallel to an orientation of the static magnetic field at the center of the at least one induction coil.

22. The surface-based NMR measurement method of claim 20, wherein the subsurface volume is a very shallow subsurface volume.

23. The surface-based NMR measurement method of claim 20, wherein the surface of the Earth comprises a surface of a man-made earthen structure.

24. The surface-based NMR measurement method of claim 20, wherein activating the NMR spectrometer components connected to the one or more electromagnetic field devices to record NMR signals produced by the precession of NMR spins comprises activating a transmit/receive switch after activating the NMR spectrometer components connected to the one or more electromagnetic field devices to transmit the radio frequency electromagnetic pulses.

25. The surface-based NMR measurement method of claim 20, wherein the at least one surface probe and the NMR spectrometer components are adapted within a portable housing or a vehicle, wherein the at least one surface probe is positioned at a bottom of the portable housing or the vehicle, and wherein positioning the at least one surface probe over the subsurface volume of interest comprises positioning the portable housing or the vehicle over the subsurface volume of interest.

26. The surface-based NMR measurement method of claim 25, further comprising moving the portable housing or the vehicle while activating the NMR spectrometer components multiple times to make multiple surface-based NMR measurements of multiple subsurface volumes as the portable housing or the vehicle moves.

27. The surface-based NMR measurement method of claim 20, further comprising activating the NMR spectrometer components to acquire at least two NMR measurements at different radio frequency electromagnetic pulse frequencies to measure subsurface volumes at different depths.

28. The surface-based NMR measurement method of claim 20, further comprising using recorded NMR signals to determine at least one of the following properties of the subsurface volume: water content, porosity, soil moisture, T1, T2, permeability bound water content, mobile water content, fluid diffusion coefficient.

29. The surface-based NMR measurement method of claim 28, further comprising activating the NMR spectrometer components to acquire at least two NMR measurements at different radio frequency electromagnetic pulse frequencies to measure subsurface volumes at different depths, and determining, for at least one of the properties, the variation of the property as a function of depth.

30. The surface-based NMR measurement method of claim 28, wherein the subsurface volume is a shallow subsurface volume.

* * * * *